United States Patent
Bal et al.

(10) Patent No.: US 9,908,101 B2
(45) Date of Patent: Mar. 6, 2018

(54) CATALYST FOR SELECTIVE DEHYDROGENATION / OXIDATIVE DEHYDROGENATION REACTIONS AND PROCESS FOR THE PREPARATION THEREOF

(71) Applicant: COUNCIL OF SCIENTIFIC & INDUSTRIAL RESEARCH, New Delhi (IN)

(72) Inventors: Rajaram Bal, Dehradun (IN); Bipul Sarkar, Dehradun (IN); Rajib Kumar Singha, Dehradun (IN); Chandrashekar Pendem, Dehradun (IN); Shubhra Acharyya Shankha, Dehradun (IN); Shilpi Ghosh, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 314 days.

(21) Appl. No.: 14/074,351

(22) Filed: Nov. 7, 2013

(65) Prior Publication Data

US 2014/0128653 A1 May 8, 2014

(30) Foreign Application Priority Data

Nov. 7, 2012 (IN) .......................... 3443/DEL/2012

(51) Int. Cl.
*B01J 23/28* (2006.01)
*B01J 37/03* (2006.01)
(Continued)

(52) U.S. Cl.
CPC ............ *B01J 23/28* (2013.01); *B01J 21/063* (2013.01); *B01J 35/002* (2013.01);
(Continued)

(58) Field of Classification Search
CPC ...... B01J 23/28; B01J 21/063; B01J 37/0018; B01J 37/035; B01J 37/082; B01J 37/10
(Continued)

(56) References Cited

U.S. PATENT DOCUMENTS 4,250,346 A  2/1981 Young
4,524,236 A  6/1985 McCain
(Continued)

FOREIGN PATENT DOCUMENTS

EP  2165997 A1  3/2010
KR  20110034146 A  *  4/2011

OTHER PUBLICATIONS

Machine translation of KR20110034146A, pulication date Apr. 2011.*

(Continued)

*Primary Examiner* — Jun Li

(74) *Attorney, Agent, or Firm* — Rick Matos; Innovar, L.L.C.

(57) ABSTRACT

The present invention provides a process and catalyst for the direct and selective conversion of ethane to ethylene. The process provides a direct single step vapor phase selective dehydrogenation/oxidative dehydrogenation of ethane to ethylene over Mo supported nanocrystalline $TiO_2$. The process provides ethane conversion of 65-96% and selectivity of ethylene up to 100%. The process may be conducted in the presence or absence of oxygen.

7 Claims, 3 Drawing Sheets

(51) Int. Cl.
  *B01J 37/08* (2006.01)
  *B01J 37/10* (2006.01)
  *B01J 21/06* (2006.01)
  *B01J 35/00* (2006.01)
  *B01J 37/00* (2006.01)
  *C07C 5/48* (2006.01)

(52) U.S. Cl.
  CPC ......... B01J 37/0018 (2013.01); B01J 37/035 (2013.01); B01J 37/082 (2013.01); B01J 37/10 (2013.01); C07C 5/48 (2013.01); *C07C 2521/06* (2013.01); *C07C 2523/28* (2013.01); *Y02P 20/52* (2015.11)

(58) Field of Classification Search
  USPC .................................. 502/309; 585/658, 661
  See application file for complete search history.

(56) References Cited

U.S. PATENT DOCUMENTS

| | | | |
|---|---|---|---|
| 6,027,775 A | 2/2000 | Kasuga | |
| 7,431,903 B2* | 10/2008 | Koyanagi | B01J 21/063 423/610 |
| 8,012,451 B2 | 9/2011 | Kobasa | |
| 8,329,139 B2 | 12/2012 | Ciccarella | |
| 2008/0031806 A1* | 2/2008 | Gavenonis | B01J 21/063 423/608 |
| 2008/0038492 A1* | 2/2008 | Huang | B82Y 30/00 428/34.1 |
| 2009/0117384 A1* | 5/2009 | Han | A61K 8/29 428/402 |
| 2009/0220561 A1* | 9/2009 | Jin | A61K 9/0009 424/423 |
| 2010/0038285 A1* | 2/2010 | Toledo Antonio | B01J 21/063 208/143 |

OTHER PUBLICATIONS

Zhou et al. ("An Integrated Process for Partial Oxidation of Alkanes" in Chem. Commun. (2003), 2294-2295).

Choudhary et al. ("Coupling of Thermal Cracking with Noncatalytic Oxidative Conversion of Ethane to Ethylene" in AIChE Journal (1997), 43(6), 1545-1550).

Heracleous et al. ("Ni—Me—O mixed metal oxides for the effective oxidative dehydrogenation of ethane to ethylene—Effect of Promoting metal Me" in J. Catalysis (2010), 270, 67-75).

Gudgila et al. ("Support Effects on the Oxidative Dehydrogenation of Ethane to Ethylene over Platinum Catalysts" in Ind. Eng. Chem. Res. (2011), 50, 8438-8443).

Sheldon et al. ("The E Factor: fifteen years on" in Green Chem. (2007), 9(12), 1273-1283).

Al-Mashta et al. ("Room temperature polymerization of ethylene on TiO2(anatase) surface; infrared spectroscopic evidence for an alkylidene-Ti4+ end-group and for a 'hydrogen-bonding' type of interaction of CH bonds of the polymer chain with the oxide surface" in J. Chem. Soc. Chem. Comm. (1983), 21, 1258-1259).

Tsilomelekis et al. ("An operando Raman study of molecular structure and reactivity of molybdenum(VI) oxide supported on anatase for the oxidative dehydrogenation of ethane", in Phys. Chem. Chem. Phys. (2012), 14(7), 2216-2228).

Martinez-Huerta et al. ("Monitoring the states of vanadium oxide during the transformation of TiO2 anatase-to-rutile under reactive environments: H2 reduction and oxidative dehydrogenation of ethane", in Cat. Comm. (Oct. 2009), 11(1), 15-19).

Wu et al. ("Growth of rutile TiO2 nanorods on TIO2 thin films on Si-based substrates" in J. Mater. Res. (2011), 26(13), 1646-1652).

* cited by examiner

CATALYST FOR SELECTIVE DEHYDROGENATION / OXIDATIVE DEHYDROGENATION REACTIONS AND PROCESS FOR THE PREPARATION THEREOF

The following specification particularly describes the invention and the manner in which it is to be performed:

CROSS-REFERENCE TO EARLIER-FILED APPLICATIONS

The present application claims the benefit of Indian application No. 3443/DEL/2012 filed Nov. 7, 2012, the entire disclosure of which is hereby incorporated by reference.

FIELD OF THE INVENTION

The present invention related to catalyst for the selective dehydrogenation/oxidative dehydrogenation of ethane to ethylene. Particularly the present invention relates to a catalyst for the vapor phase dehydrogenation/oxidative dehydrogenation of ethane to ethylene under atmospheric pressure. More particularly, the present invention relates to a process future to produce ethylene from ethane with high conversion and selectivity in one single step. The present invention relates to an improved process for the preparation of Mo supported nanocrystalline $TiO_2$; the catalyst can effectively produce ethylene without any deactivation in a longer run.

BACKGROUND OF THE INVENTION

Ethylene is a very important chemical, which does not occur in nature but still represents the organic chemicals consumed in the greater quantity worldwide. It is mainly the raw material for a large no of industrial products, such as poly-ethylene, polyvinyl chloride, polystyrene, polyester etc. Despite of the economic uncertainty around the petrochemical industry, ethylene production and consumption scenario are expected to grow continuously. The global demand of ethylene is over 140 million tons per year with the future growth rate of 3.5% per year (www.technip.com/sites/default/files/technip/publications/attachments/-Ethylene_production_1.pdf). Industrially, ethylene is produced by steam cracking of ethane; reactors have to plug into a firebox as the cracking of ethane is endothermic in nature. In standard condition a steam cracker can achieve up to 60% of ethane conversion with maximum 80% ethylene selectivity. However, oxidative dehydrogenation (ODH) is one of the alternative processes mainly known. Since, oxidative dehydrogenation is exothermic so the reaction goes automatically as the catalyst is light off. While, ODH can offers high conversion with high ethylene selectivity, minimizing the contact time in milliseconds.

In this context, oxidative dehydrogenation (ODH) will have the clear future to replace steam cracker to produce ethylene. Although many researcher has reported oxidative dehydrogenation of ethane in resent past, but poor atom efficiency (called E-factor by R A Sheldon in Chemistry & Industry, 6 Jan. 1997, P 13) in respect to both conversion and selectivity restrict the successful commercialization of ODH process. Moreover, the use of pure oxygen in ODH process makes the process cost high; hence to deploy ODH reactor industry must put a costly gas separation tower first. In this context catalytic dehydrogenation is another possibility to replace the existing processes of ethylene production, as it can deliver ≥80% ethane conversion with ≥90% ethylene conversion. Uses of solid nanocrystalline metal oxides catalyst are very important as they offer larger active surface area with option to reuse.

There are many reports on the dehydration as well as oxidative dehydrogenation (ODH) of ethane over different solid catalyst, but to the best of our knowledge there is no reference available that can offer such atom efficiency for a prolonged reaction time.

Reference can be made to European patent EP 2165997 A1, 2010 wherein Han et al. provided a novel one step catalytic process of oxidative dehydrogenation of ethane for the production of ethylene and carbon dioxide using pure oxygen over Fe-manganese oxide or Fe—$CaCO_3$ catalyst. But use of pure oxygen at a temperature≥600° C. is very much painful, because above 600° C., thermal cracking will come into effect. So use of pure oxygen at above 600° C. makes the process cost higher and unfavourable for commercialization.

Reference can be made to U.S. Pat. No. 4,250,346, 1981 by Young et al. In their patent application, they claimed gas phase oxidative dehydrogenation of ethane in presence or absence of $H_2O_2$ over mix-Molybdenum oxide catalyst ($Mo_a$ $X_b$ $Y_c$) (where X=Cr, Mn, Nb, Ta, Ti, V, W and Y=Bi, Ce, Co, Cu, Fe, Mg, K, Ni, P etc.) at ≤500° C. The drawbacks of this process are the low conversion of butane (only 2 to 8% of ethane conversion was claimed) although the process operates at 1-30 atmosphere pressure. Again, the use of $H_2O$ rise the question of metal leaching from the solid catalyst, leads to rapid deactivation of catalyst.

Reference can be made to the article AIChE journal, 1997, 43, 1545-1550 in which Choudhary et al. studied non-catalytic thermal cracking of ethane in presence of oxygen in a space velocity of 2000-11000 $h^{-1}$. But, the conversion of ethane is only 44.2% whereas in absence of oxygen is further decreases to 28.5%. Moreover, the selectivity of ethylene goes down as the side reaction product (such as $CH_4$, $C_3H_6$, $C_3H_8$ etc.) are predominates at 800° C.

Reference can be made to the U.S. Pat. No. 4,524,236 by McCain et al. in which they developed one step low temperature oxidative dehydrogenation of ethane to produce ethylene over mixed oxide catalyst with 1:1.2 oxygen to ethane as feed. The main drawback of the process is the low space velocity, loss of selectivity (about 11% selectivity decreased as the conversion goes up from 53% to 76%). The low space velocity makes the industrial difficult, as the industry need process which can give steady conversion and selectivity in a high space velocity in order to cut down the production cost.

Reference can be made to the J. Catal., 2010, 270, 67-75 wherein Lemoniou et al. reported low temperature oxidative dehydrogenation of ethane to ethylene over Ni—Me—O (where Me is the doped metal) as catalyst. Under the reported process 46% ethylene yield at 400° C. has been achieved with Ni—Nb—O catalyst.

Reference may also be made to Chem. Comm., 2003, 18, 2294-2295, in which partial oxidation of ethane was carried out via bromination followed by reaction with mix metal oxide. A product selectivity of ≥80% was achieved over $Co_2O_4$:$ZrO_2$ catalyst. But main drawback is the use of bromine and double stage reactor setup to achieve such high product selectivity.

Another reference can be made to Ind. Eng. Chem. Res., 2011, 50, 8438-8442, by Leclerc et al. on the ODH of ethane over platinum catalyst. Wherein, silica supported platinum catalyst demonstrate the highest conversion of 76% with ethylene yield of 46% at 900° C. with $C_2H_6/O_2$ ratio of 1.5.

OBJECTS FOR THE INVENTION

Main object of the present invention is to provide a catalyst for the selective dehydrogenation/oxidative dehydrogenation of ethane to ethylene.

Another object of the present invention is to provide an improved process for the preparation of catalyst for the selective dehydrogenation/oxidative dehydrogenation of ethane to ethylene.

Yet another object of the present invention is to provide a process for the vapor phase dehydrogenation/oxidative dehydrogenation of ethane to ethylene under atmospheric pressure.

Yet another object of the present invention is to provide a process future to produce ethylene from ethane with high conversion and selectivity in one single step.

Yet another object of the present invention is to provide an efficient Mo supported nanocrystalline $TiO_2$; the catalyst can effectively produce ethylene without any deactivation in a longer run.

SUMMARY OF THE INVENTION

Accordingly, present invention provides Mo—$TiO_2$ nanocrystalline oxide catalyst wherein Mo is in the range of 5 to 15 wt % and $TiO_2$ in the range of 85 to 95 wt % having particle size in the range of 80-150 nm.

In an embodiment of the present invention, Mo—$Ti_{O2}$ nanocrystalline oxide catalyst as claimed in claim 1, wherein said catalyst is useful for production of ethylene from ethane by vapor phase dehydrogenation/oxidative dehydrogenation in absence and presence of oxygen.

In an embodiment, present invention provides a process for the preparation of Mo—$TiO_2$ nanocrystalline oxide catalyst as used in claim 1 and the said process comprising the steps of:
i. mixing titanium isopropoxide Ti(i-Pr)$_4$, ethanol and octadecyldimethyl (3-trimethoxy silylpropyl) ammonium chloride in the ratio ranging between 50:3500:1 to 100:3500:1 followed by adjusting pH between 3-10 to obtain mixed solution;
ii. heating mixed solution as obtained in step (i) at temperature in the range of 70 to 90° C. for period in the range of 1 to 2 h;
iii. autoclaving the solution as obtained in step (ii) at a temperature in the range of 150 to 200° C. hydrothermally for period in the range of 20 to 30 h;
iv. filtering, washing and drying the autoclaved solution as obtained in step (iii) at a temperature in the range of 100 to 130° C. for period in the range of 10 to 18 h;
v. calcining the materials as obtained in step (iv) at temperature in the range of 300 to 800° C. for period in the range of 4 to 6 h in air to yield solid $TiO_2$;
vi. mixing MoCl$_3$, cetyltrimethylammonium bromide and hydrazine in the molar ratio of Mo, CTAB and Hydrazine ranging between 1:1:0.01 to 1:2:0.01 followed by adding $TiO_2$ as obtained in step (v) maintaining weight ratio of Mo to $TiO_2$ in the range of 0.05 to 0.15;
vii. stirring the mixture as obtained in step (vi) for period in the range of 2 to 5 h, filtering followed by drying the materials in oven at a temperature ranging between 100 to 130° C. for period in the range of 10 to 18 h;
viii. calcining the material at temperature in the range of 300 to 800° C. for period in the range of 4 to 6 h in air to yield Mo—$TiO_2$ nanocrystalline oxide catalyst.

In another embodiment, present invention provides a process for the production of ethylene from ethane by vapor phase dehydrogenation/oxidative dehydrogenation in absence and presence of oxygen using Mo—$TiO_2$ nanocrystalline oxide catalyst and the said process comprising the steps of:
i. passing ethane at atmospheric pressure, at a temperature range of 550-850° C. with a gas hourly space velocity (GHSV) in the range of 5000-70000 ml g$^{-1}$ h$^{-1}$ in the presence or absence of molecular oxygen as feed and helium as carrier over Mo supported $TiO_2$ catalyst with Mo to $TiO_2$ weight ratio varied between 0.03 to 0.2 for a period of 1-20 hours to obtain desired product ethylene.

In yet another embodiment of the present invention, reaction temperature is preferably in the range 650 to 800° C.

In yet another embodiment of the present invention, gas hourly space velocity (GHSV) is preferably in the range of 10000 to 50000 ml g$^{-1}$ h$^{-1}$.

In yet another embodiment of the present invention, the reaction time used is preferably in the range 3 to 20 h.

In yet another embodiment of the present invention, the conversion percentage of ethane is in the range of 65 to 96 mol %.

In yet another embodiment of the present invention, the selectivity of the ethylene obtained in the range of 88 to 100 mol %.

BRIEF DESCRIPTION OF THE INVENTION

DETAILED DESCRIPTION OF THE INVENTION

Figure 1:
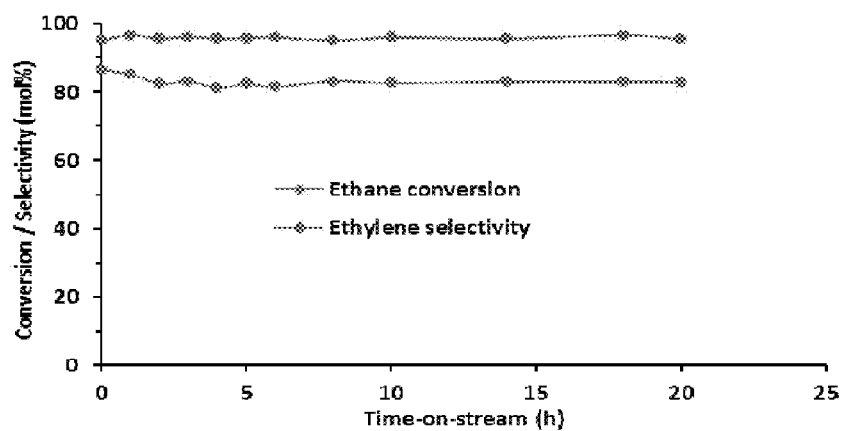
FIG. 1 represents the conversion of ethane to ethylene over time on stream for the Mo—$TiO_2$ catalyst.
Figure 2:
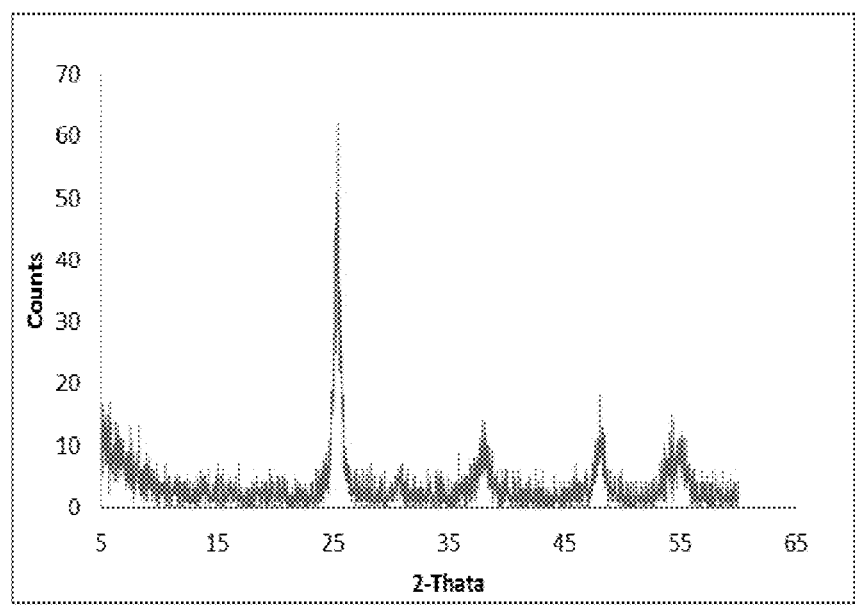
FIG. 2 represents X-ray Diffraction (XRD) pattern of the prepared catalyst.
Figure 3:
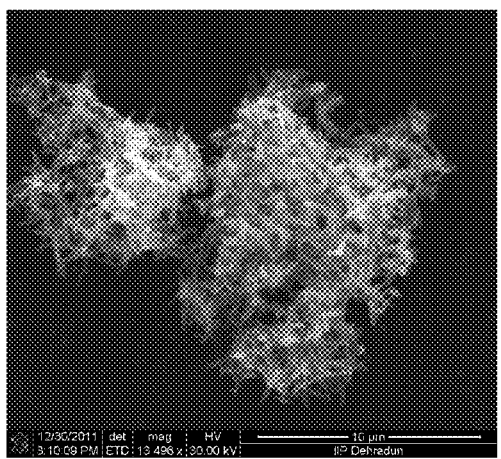
FIG. 3 represents Scanning Electron Microscope (SEM) images of the prepared Mo—TiO2 catalysts.
Figure 3:
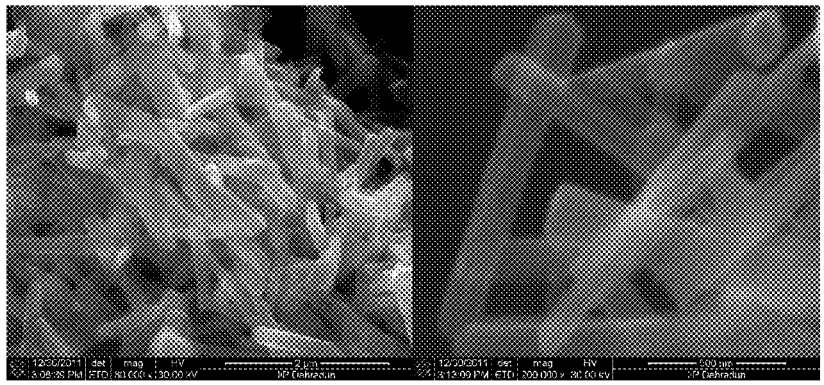

Present invention provides a catalyst consisting of Mo—$TiO_2$ prepared hydrothermally and process to produce ethylene from ethane by gas phase dehydrogenation/oxidative dehydrogenation with and without $O_2$ over Mo—$TiO_2$ catalyst at atmospheric pressure, at a temperature range of 550 to 850° C. with a gas hourly space velocity (GHSV) in the range of 5000-70000 ml g$^{-1}$ h$^{-1}$ in the presence of Mo supported $TiO_2$ catalyst with Mo to $TiO_2$ weight ratio varied between 0.03 to 0.2 to obtain desired product ethylene for a period of 1-20 hours.

The present invention provides a process for the production of ethylene from ethane by vapor phase dehydrogenation/oxidative dehydrogenation in absence and presence of oxygen and Mo—$TiO_2$ nanocrystalline oxide as the catalyst which involves the following steps:
i. Synthesis of $TiO_2$ oxide using sol composition of Ti(i-Pr)$_4$, octadecyldimethyl (3-trimethoxy silylpropyl) ammonium chloride, 1N NaOH solution to adjust the pH between 3-10;
ii. heated at 80° C. and maintained for 1-2 h;

iii. Transferring the solution into an closed Teflon line stainless steel autoclave and heating the solution inside the oven in the temperature range between 150-200° C. hydrothermally for 20-30 h;

iv. filtered the material by washing with excess water (2 liter) followed by drying the materials in oven at a temperature between 100-130° C. for 10-18 h;

v. Calcination of the materials at 300-800° C. for 4-6 h in air to yield solid TiO2;

vi. Synthesis of Mo—$TiO_2$ catalyst using ethanol medium taking the solution composition of $MoCl_3$, cetyltrimethylammonium hydrazine, in the molar ratio of Mo:CTAB:Hydrazine=1:1:0.01 and prepared $TiO_2$;

vii. The weight ratio of Mo to $TiO_2$ varied in the range of 0.05 to 0.15;

viii. Stirring the mixture for 2-5 h followed and filtered the material by washing with excess water (2 liter) followed by drying the materials in oven at a temperature between 100-130° C. for 10-18 h;

ix. Calcination of the materials at 300-800° C. for 4-6 h in air to yield Mo—TiO2;

x. Dehydrogenation/oxidative dehydrogenation of ethane was carried out in a fixed bed down-flow reactor using ultra-pure ethane and/or molecular oxygen as feeds and helium as carrier for 1-20 h to yield ethylene;

xi. The process pressure was kept at 1 atmosphere;

xii. The reaction temperature is preferably in the range 650 to 800° C.;

xiii. The gas hourly space velocity (GHSV in ml $g^{-1}$ $h^{-1}$) is preferably in the range 10000 ml g−1 h−1 to 50000 ml g−1 h−1;

xiv. The ethane conversion (mol %) of 65-96% is obtained and selectivity (mol %) to ethylene is 78 to 100%.

The detailed steps of the process are:

The dehydrogenation of ethane was carried out in a fixed-bed down flow reactor at atmospheric pressure. Typically 200 mg of catalyst was placed in between two quartz wool plugged in the centre of the 6 mm quartz reactor and dehydrogenation of ethane was carried out in a temperature range of 650-800° C. The catalyst was reduced using 5% $H_2$ balance He at 650° C. for 1 h before the reaction. The gas hourly space velocity (GHSV) was varied between 5000 ml $g^{-1}$ $h^{-1}$ to 50000 ml $g^{-1}$ $h^{-1}$ with a molar ratio of $C_2H_6$:$O_2$:He of 1:1:8. The reaction products were analyzed using an online gas chromatography (Agilent 7890A) fitted with a FID & TCD detector using $Al_2O_3$/KCl column (to analyse $C_2H_6$, $C_2H_4$, $CH_4$ etc.) and PoraPack-Q (for analyzing $O_2$ and $CO_2$).

An improved process for the preparation of Mo—TiO2 catalyst, wherein the said process comprising the steps of:

a) Mixing the chemicals: Ti(i-Pr)$_4$, octadecyldimethyl (3-trimethoxy silylpropyl) ammonium chloride and 1N NaOH solution to adjust the pH between 3-10.

b) Heating the solution at 80° C. and maintained for 1-2 h c) Transferring the solution into a closed Teflon line stainless steel autoclave and heating the solution inside the oven in the temperature range between 150-200° C. hydrothermally for 20-30 h.

d) filtered the material by washing with excess water (2 liter) followed by drying the materials in oven at a temperature between 100-130° C. for 10-18 h e) Calcination of the materials at 300-800° C. for 4-6 h in air to yield solid $TiO_2$.

f) Synthesis of Mo—$TiO_2$ catalyst using ethanol medium taking the solution composition of $MoCl_3$ cetyltrimethylammonium bromide, hydrazine, in the molar ratio of Mo:CTAB:Hydrazine=1:1:0.01 and prepared $TiO_2$ g) The weight ratio of Mo to $TiO_2$ varied in the range of 0.05 to 0.15 h) Stirring the mixture for 2-5 h followed and filtered the material by washing with excess water (2 liter) followed by drying the materials in oven at a temperature between 100-130° C. for 10-18 h i) Calcination of the materials at 300-800° C. for 4-6 h in air to yield Mo—$TiO_2$ A process for gas phase dehydrogenation/oxidative dehydrogenation with and without $O_2$ of ethane to produce ethylene using catalyst comprising the steps of:

I. Passing ethane at atmospheric pressure, at a temperature range of 550-850° C. with a gas hourly space velocity (GHSV) in the range of 5000-70000 ml $g^{-1}$ $h^{-1}$ in the presence of Mo supported $TiO_2$ catalyst with Mo to $TiO_2$ weight ratio varied between 0.03 to 0.2 to obtain desired product ethylene for a period of 1-20 hours.

Weight ratio of Mo to $TiO_2$ of the catalyst varied in the range of 0.05 to 0.15.

Reactor pressure is preferably in the range of 1 atmosphere. Reaction temperature is preferably in the range 650 to 800° C. Gas hourly space velocity (GHSV) is preferably in the range of 1000 g $ml^{-1}$ $h^{-1}$ to 50000 g $ml^{-1}$ $h^{-1}$. Reaction time used is preferably in the range 3-20 h. Conversion (mol %) of ethane is in the range of 65 to 96%. Selectivity (mol %) of the ethylene obtained in the range of 78 to 100%.

EXAMPLES

The following examples are given by way of illustration and therefore should not be construed to limit the scope of the invention.

Example 1: Synthesis of $TiO_2$ 5 ml titanium isopropoxide was taken in 75 ml chilled ethanol to form a heterogeneous solution. Approximately 0.2 g octadecyldimethyl (3-trimethoxy silylpropyl) ammonium chloride was added drop wise under vigorous stirring. Then, the pH of the mixed solution was adjusted by 1(M) NaOH solution and pH of the mixed solution was fixed at 10. Finally, the mixed solution was heated at 80° C. and maintained for 2 h. The resultant mixture was autoclaved at 180° C. for 24 h for further crystallization. The white precipitate ($TiO_2$) was collected by filtration, washed thoroughly with distilled water and ethanol and dried at 80° C. for 12 h. To remove the template the as-synthesized material was heated to 750° C. with a temperature ramp of 1.5° C./min under static air and kept at the same temperature for 4 h. This was used as a $TiO_2$ support material.

Synthesis of Mo—$TiO_2$

Synthesis of Mo—$TiO_2$ catalyst using ethanol (25 ml) medium taking the solution composition of 1.05 g of $MoCl_3$, 0.5 g of cetyltrimethylammonium bromide, 0.2 g hydrazine (the molar ratio of Mo:CTAB:Hydrazine=1:1:0.01) and prepared 1.0 g of $TiO_2$ was added to it such a way that the weight ratio of Mo to $TiO_2$ was 0.05. The mixture was stirred for 3 h and the solid material was filtered out with 2 liter distilled water and it was dried in the oven at 110° C. for 16 h. Finally the calcination of the material was carried out at 750° C. for 6 h in air.

The X-ray diffraction pattern, Scanning Electron Microscope (SEM) images and Transmission Electron Microscope (TEM) images of this material are given below.

Example 2

This example describes the dehydrogenation of ethane by gas phase reaction in He using Mo—$TiO_2$ nanocrystalline oxide as the catalyst. (Table-1)

The dehydrogenation of ethane to ethylene was carried out in a fixed-bed down flow quartz reactor at atmospheric pressure. Typically 200 mg of catalyst was placed in between two quartz wool plugged in the center of the 6 mm quartz reactor and dehydrogenation of ethane was carried out in a temperature range of 650-800° C. The gas hourly space velocity (GHSV) was varied between 10000 ml $g^{-1}$ $h^{-1}$ to 30000 ml $g^{-1}$ $h^{-1}$ with a molar ratio of $C_2H_6$:He of 1:9.

Process Conditions
Catalyst: 0.2 g
Mo: $TiO_2$ wt % in the catalyst=5%
Pressure: 1 atmosphere
Total flow=33.3 ml/min (GHSV=10000)
Reaction time: 1 h

TABLE 1

| Catalyst (5% Mo—$TiO_2$) | Temperature (° C.) | Ethane Conversion (mol %) | Ethylene Selectivity (mol %) | Yield (%) |
|---|---|---|---|---|
| Oxidative dehydrogenation (With $O_2$) | 750 | 91 | 84 | 76 |
| dehydrogenation (Without $O_2$) | 750 | 86 | 95 | 82 |

Example 3

The example describes the effect of temperature on yield and selectivity ethylene. The product analysis presented in Table-2.

Process Conditions:
Catalyst: 0.2 g
Mo: $TiO_2$ wt % in the catalyst=5%
Pressure: 1 atmosphere
Total flow=33.3 ml/min (GHSV=10000)
Reaction time: 1 h

TABLE 2

Effect of temperature on ethane conversion, ethylene yield and selectivity

| | Temperature (° C.) | Ethane Conversion (mol %) | Ethylene Selectivity (mol %) | Yield (%) |
|---|---|---|---|---|
| Oxidative dehydrogenation (With $O_2$) | 650 | 65 | 89 | 58 |
| | 700 | 82 | 87 | 71 |
| | 750 | 91 | 84 | 76 |
| | 800 | 96 | 78 | 74 |
| dehydrogenation (Without $O_2$) | 650 | 10 | 100 | 10 |
| | 700 | 56 | 97 | 54 |
| | 750 | 86 | 95 | 82 |
| | 800 | 94 | 89 | 84 |

Example 4

The example describes the effect of time on stream on yield and selectivity of ethylene. The product analysis presented in Table 3

Process Conditions:
Catalyst: 0.2 g, Mo: $TiO_2$ wt % in the catalyst=5%
Pressure: 1 atmosphere
Total flow=33.3 ml/min (GHSV=10000)
Reaction temperature: 750° C.

Example 5

The example describes the effect of gas hourly space velocity (GHSV) on yield and selectivity of ethylene. The product analysis presented in Table-3.

Process Conditions:
Catalyst: 0.2 g
Mo: $TiO_2$ wt % in the catalyst=5%
Pressure: 1 atmosphere
Reaction temperature: 750° C.
Reaction time: 1 h

TABLE 3

Effect of gas hourly space velocity (GHSV) on ethane conversion, ethylene yield and selectivity

| | GHSV (ml $g^{-1}$ $h^{-1}$) | Ethane Conversion (mol %) | Ethylene Selectivity (mol %) | Yield (%) |
|---|---|---|---|---|
| Oxidative dehydrogenation (With $O_2$) | 10000 | 91 | 84 | 76 |
| | 15000 | 76 | 84 | 64 |
| | 20000 | 63 | 86 | 54 |
| | 25000 | 54 | 87 | 47 |
| | 30000 | 48 | 89 | 43 |
| dehydrogenation (Without $O_2$) | 10000 | 86 | 95 | 82 |
| | 15000 | 79 | 96 | 76 |
| | 20000 | 63 | 97 | 61 |
| | 25000 | 52 | 98 | 51 |
| | 30000 | 41 | 100 | 41 |

Advantages of the Invention

The main advantages of the present invention are:
1. The process of the present invention converts ethane to ethylene in a single step with a single catalyst.
2. The process provides not only good conversion but also good selectivity for ethylene.
3. The process produce nominal by-product in the form of methane which is also a major advantage of this process.
4. The process does not need any addition reagent (such as chlorine, bromine etc.) to generate active species.
5. The catalyst is used in very low amounts.
6. The catalyst does not deactivate till 20 h with the reaction stream.

Figure 4:
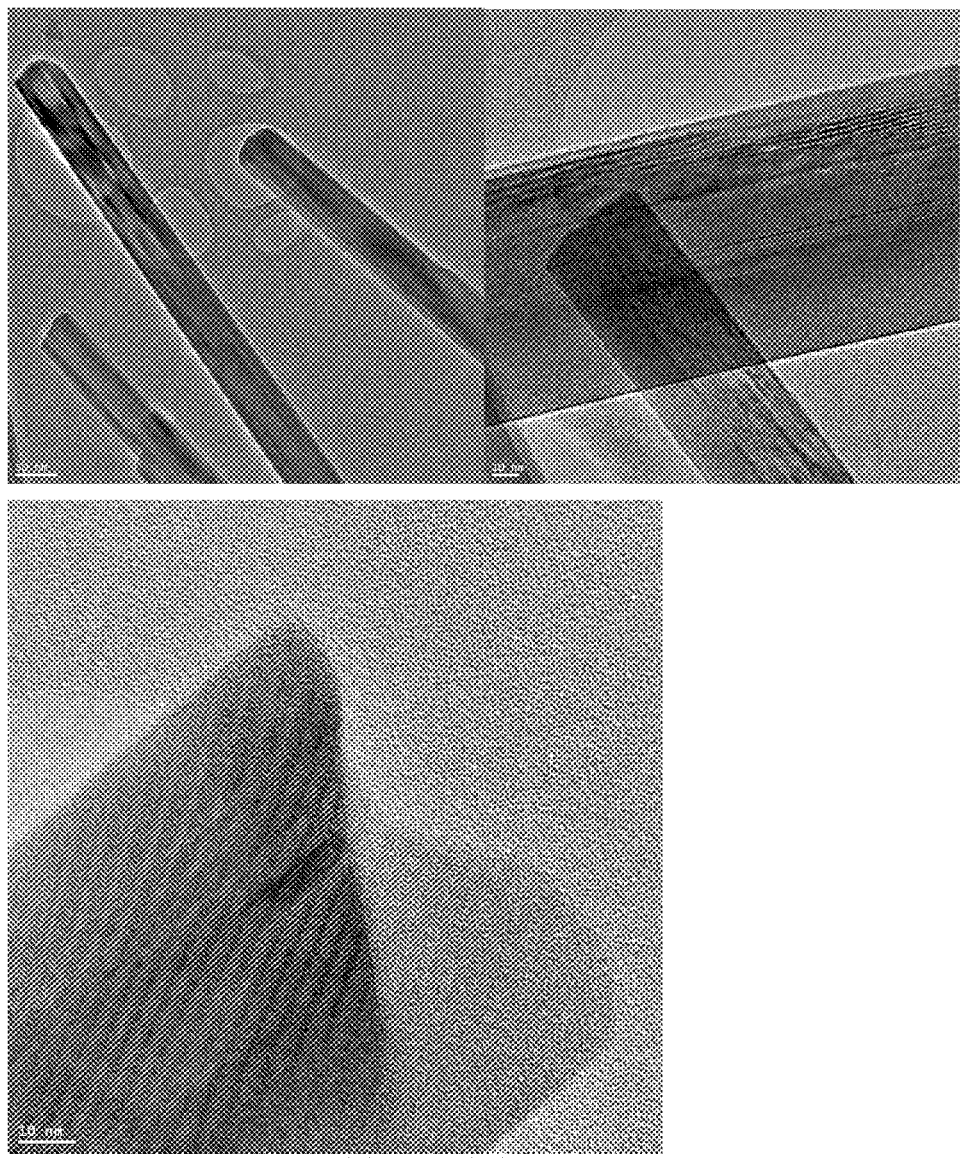
FIG. 4 represents Transmission Electron Microscope (TEM) images of the prepared catalyst.

The invention claimed is:
1. A Mo—$TiO_2$ nanocrystalline oxide catalyst, wherein Mo is present in the range of 5 wt % to 15 wt % and $TiO_2$ is present in the range of 85 wt % to 95 wt %, the catalyst having particle size in the range of 80-150 nm, and wherein said catalyst is able to selectively convert ethane to ethylene by vapor phase dehydrogenation/oxidative dehydrogenation in the absence or presence of oxygen, respectively, and wherein the catalyst exhibits a crystal morphology as depicted in the transmission electron microscope image of FIG. 4.

2. The catalyst of claim 1, wherein the catalyst has been prepared according to a process comprising:
   a. preparing solid $TiO_2$ from a mixture of titanium isopropoxide $Ti(i-Pr)_4$ and octadecyldimethyl (3-trimethoxy silylpropyl) ammonium chloride, present in the ratio ranging from 50:3500:1 to 100:3500:1, in liquid, wherein the mixture has been heated at a temperature in the range of 70 to 90° C. and then autoclaved at a temperature in the range of 150 to 200° C. to form a liquid containing solid material, wherein the solid material is separated from the liquid and then calcined at a temperature in the range of 300 to 800° C. in air to yield the solid $TiO_2$; and
   b. mixing $MoCl_3$, cetyltrimethylammonium bromide and hydrazine, at a molar ratio of Mo:CTAB:hydrazine ranging from 1:1:0.01 to 1:2:0.01, in a liquid followed by adding the $TiO_2$, a weight ratio of Mo to $TiO_2$ in the range of 0.05 to 0.15, to form a mixture comprising a solid material that is separated and then calcined at a temperature in the range of 300 to 800° C. in air to yield the Mo—$TiO_2$ nanocrystalline catalyst.

3. The catalyst of claim 1, wherein the catalyst comprises:
   a. $TiO_2$ prepared from a mixture of titanium isopropoxide $Ti(i-Pr)_4$ and octadecyldimethyl (3-trimethoxy silylpropyl) ammonium chloride, present in the ratio ranging from 50:3500:1 to 100:3500:1, wherein the $TiO_2$ has been calcined at a temperature in the range of 300 to 800° C. in air; and
   b. Mo support prepared from a mixture of $MoCl_3$, cetyltrimethylammonium bromide and hydrazine, at a molar ratio of Mo:CTAB:hydrazine ranging from 1:1:0.01 to 1:2:0.01, and the $TiO_2$, wherein the weight ratio of Mo to $TiO_2$ in the catalyst is in the range of 0.05 to 0.15, and the catalyst has been calcined at a temperature in the range of 300 to 800° C. in air.

4. The catalyst of claim 3, wherein the catalyst comprises:
   a. $TiO_2$ prepared from a mixture of titanium isopropoxide $Ti(i-Pr)_4$ and octadecyldimethyl (3-trimethoxy silylpropyl) ammonium chloride, present in the ratio ranging from 50:3500:1 to 100:3500:1, in liquid, wherein the mixture has been heated at a temperature in the range of 70 to 90° C. and then autoclaved at a temperature in the range of 150 to 200° C. to form a liquid containing solid material, wherein the solid material is separated from the liquid and then calcined at a temperature in the range of 300 to 800° C. in air to yield the solid $TiO_2$; and
   b. the Mo support has been prepared by from a mixture of $MoCl_3$, cetyltrimethylammonium bromide and hydrazine, at a molar ratio of Mo:CTAB:hydrazine ranging from 1:1:0.01 to 1:2:0.01, in a liquid followed by addition of the $TiO_2$ at a weight ratio of Mo to $TiO_2$ in the range of 0.05 to 0.15, to form a mixture comprising a solid material that is separated and then calcined at a temperature in the range of 300 to 800° C. in air to yield the catalyst.

5. The catalyst of claim 1, wherein the catalyst is able to selectively convert ethane to ethylene by vapor phase dehydrogenation/oxidative dehydrogenation in the absence or presence of oxygen, respectively, and wherein the conversion percentage of ethane is in the range of 65 mol % to 96 mol %, and the selectivity of the ethylene conversion in the range of 88 mol % to 100 mol %.

6. The Mo—$TiO_2$ nanocrystalline oxide catalyst of claim 1, wherein the catalyst is an anatase nanocrystalline catalyst.

7. A Mo—$TiO_2$ nanocrystalline oxide anatase catalyst, wherein Mo is present in the range of 5 wt % to 15 wt % and $TiO_2$ is present in the range of 85 wt % to 95 wt %, the catalyst having particle size in the range of 80-150 nm, wherein said catalyst is able to selectively convert ethane to ethylene by vapor phase dehydrogenation/oxidative dehydrogenation in the absence or presence of oxygen, respectively, wherein the conversion percentage of ethane is in the range of 65 mol % to 96 mol %, and the selectivity of the ethylene conversion in the range of 88 mol % to 100 mol %, and wherein the catalyst exhibits a crystal morphology as depicted in the transmission electron microscope image of FIG. 4.

* * * * *